(12) United States Patent
Kranzmann et al.

(10) Patent No.: US 7,905,150 B2
(45) Date of Patent: Mar. 15, 2011

(54) INSPECTION FIXTURE FOR THE SIMULTANEOUS ADMISSION OF A DISK-SHAPED TEST SPECIMEN WITH A SEARCH GAS AND A MECHANICAL LOAD AS WELL AS PERTINENT TESTING METHOD

(75) Inventors: Axel Kranzmann, Berlin (DE); Daniela Hünert, Berlin (DE)

(73) Assignee: Bam Dundesanstalt fuer Materialforschung und-Pruefung, Berlin (DE)

( * ) Notice: Subject to any disclaimer, the term of this patent is extended or adjusted under 35 U.S.C. 154(b) by 56 days.

(21) Appl. No.: 12/178,596

(22) Filed: Jul. 23, 2008

(65) Prior Publication Data

US 2009/0031820 A1 Feb. 5, 2009

(30) Foreign Application Priority Data

Jul. 30, 2007 (DE) .......................... 10 2007 035 917

(51) Int. Cl.
*G01N 3/00* (2006.01)
*G01M 3/04* (2006.01)

(52) U.S. Cl. ............................................. 73/807; 73/40

(58) Field of Classification Search .................... 73/856, 73/40, 40.5, 807
See application file for complete search history.

(56) References Cited

FOREIGN PATENT DOCUMENTS

| | | |
|---|---|---|
| DE | 53351 A1 | 2/1890 |
| DE | 2728838 A1 | 1/1979 |
| DE | 2802645 A1 | 7/1979 |
| DE | 29717736(U1) | 5/1998 |
| DE | 10242789 B3 | 4/2004 |
| GB | 2012971 A | 8/1979 |

*Primary Examiner* — Lisa M Caputo
*Assistant Examiner* — Jonathan Dunlap
(74) *Attorney, Agent, or Firm* — Perkins Coie LLP

(57) ABSTRACT

The invention relates to a test device for simultaneously exposing a disk-shaped test specimen to a flowing and pressurized test gas and mechanical load as well as an associated test method. The test device is comprised of the following components: a specimen seat, which is designed in such a way that an edge area of the test specimen rests on the specimen seat and an inner area of the test specimen is accessible from its upper side and lower side; a ram arranged above the specimen seat, with which a presettable mechanical load can be exerted on the upper side of the test specimen; and a gas feed plate arranged beneath the specimen seat, with which the test gas can be conveyed to the lower side of the test specimen.

20 Claims, 1 Drawing Sheet

INSPECTION FIXTURE FOR THE SIMULTANEOUS ADMISSION OF A DISK-SHAPED TEST SPECIMEN WITH A SEARCH GAS AND A MECHANICAL LOAD AS WELL AS PERTINENT TESTING METHOD

TECHNICAL FIELD

The invention relates to a test device for simultaneously exposing a disk-shaped test specimen to a flowing and pressurized test gas and mechanical load as well as an associated test method.

BACKGROUND

Components made of the greatest variety of materials are frequently subject in practice to high mechanical loads in the presence of corrosively flowing gases under pressure. Examples of these types of components include gas turbine blades, compressors, pipelines and $CO_2$ injectors for oil and gas producing facilities for developing oil or gas fields. The first time new or even known materials are used in these types of components requires an assessment of the risk of failure. Previous design methods utilize characteristic values, which are derived from pure mechanical tests and pure corrosive tests. For the most part, the results are combined in such a way that the material loss or the weakening from gas erosion and gas corrosion is computed over time and a mechanical property with a risk factor is assigned to the residual material strength. This method fails when the material changes its mechanical properties or loses strength more intensely than provided for in the risk factor. The method can fail in particular if there is positive feedback between the mechanical load and the corrosion, i.e., the rate of corrosion increases under load. In the case of pressurized systems, a dependence on the total pressure is also observed. A consequence of the limitations of the known test methods is that for safety reasons the full potential of the materials used is not incorporated in the calculation of the risk of failure.

Standardized corrosion tests with simultaneous mechanical superimposition are known, in which bending or tensile stresses are observed in a corrosive fluid medium. Moreover, there are test methods that can determine a temperature-dependence of the corrosion rate. As is known, superimposing temperature, tension and load can be recorded in tensile or bending tests. Known test devices and associated test methods have other disadvantages depending on the design and application, such as:

- For the most part, an additional total pressure can be applied from inside only in hollow test specimens. Manufacturing these types of test specimens is very cost-intensive.
- Often the selection of the corrosive media is severely limited by the procedural steps for mechanical load initiation and the specimen holder.
- Special test specimens, which are very expensive to manufacture, are used in standardized tensile tests.
- Often the test specimens are heated. As a rule, this does not correspond to the technical application, for example in the case of containers and pipes.
- Because of reactor walls and/or voluminous furnace devices there are only slow cooling rates.
- The corrosively stressed specimen holders must be cooled intensively so that they themselves do not corrode.

The objective of the present invention is making available a test device and a test method, which overcomes one or more of the described disadvantages of the prior art and allows improved assessment of the risk of failure of components, which are simultaneously exposed to corrosive processes and mechanical load.

SUMMARY OF THE INVENTION

A first aspect of the invention lies in providing a test device for simultaneously exposing a disk-shaped test specimen to a flowing and pressurized test gas and mechanical load. The inventive test device is comprised of the following components:

- a specimen seat, which is designed in such a way that an edge area of the test specimen rests on the specimen seat and an inner area of the test specimen is accessible from its upper side and lower side;
- a ram arranged above the specimen seat, with which a presettable mechanical load can be exerted on the upper side of the test specimen (12); and
- a gas feed plate arranged beneath the specimen seat, with which the test gas can be conveyed to the lower side of the test specimen.

With the aid of the inventive test device it is possible for the first time to test the simultaneous impact of mechanical load and gas erosion or gas corrosion in a defined manner. Among other things, the test device relies on a standardizable, flat shape of the test specimen, which can be manufactured easily and cost-effectively in the case of many materials. The surface of the disk-shaped test specimens can also bear coatings as the case may be.

The inventive test device is comprised accordingly of means for simultaneously exposing the test specimen to a pressurized test gas (a potentially corrosive gas) and mechanical load. In addition, however, additional parameters of the test method can also be varied, e.g., total pressure, temperature of the test specimen or temperature of the test gas, flow rate of the gas over the test specimen. The test device means required to do this will be described in greater detail further below.

According to a preferred embodiment, the specimen seat, the ram and the gas feed plate are arranged in the interior of a pressure-resistant test container. In other words, the test device is designed to execute test methods in which superatmospheric pressure is in effect in the interior of the test container. For example, the test device is designed for test methods under a pressure of up to 350 bar. As a result, the pressure in the interior of the test container is available as an adjustable parameter for the test method.

The test container preferably has a double jacket as an outer shell that can be permeated by a coolant. If the double jacket is coupled for example to a thermostat, the temperature can be controlled in the interior via the circulating coolant.

The inventive specimen seat is designed in such a way that an edge area of the test specimen rests on the specimen seat and an inner area of the test specimen is accessible from its upper side and lower side. In other words, the test specimen is held only on its edges in the position required for executing the test method. The entire inner area of the test specimen is available for load initiation and exposure of the test gas.

The test device preferably contains a lower shell, which accommodates the gas feed plate, and the specimen seat includes rolling elements made of an inert material sitting on an edge of the lower shell. According to this embodiment, it is also provided that the test specimen be placed on the lower shell, which is arranged in the interior of the test device. In this case, the test specimen lies on top of the edge of the lower shell, more precisely on a plurality of rolling elements arranged in this area. These rolling elements are comprised of an inert material and are designed in such a way that, in the case of mechanical load initiation via the ram, the test specimen is pulled further into the interior of the lower shell as a result of the bending load and in the process slides on the rolling elements.

According to a preferred variation of the preceding embodiment, the test device also contains an upper shell, which accommodates the ram, and the specimen seat includes rolling elements made of an inert material sitting on an edge of the upper shell. The geometry and material selection of the rolling elements on the upper shell can be specified in a manner that is analogous to the corresponding rolling elements of the lower shell. The rolling elements of the upper shell still allow a sliding of the test specimen in the case of a bending load by the ram. The objective of the upper rolling elements, however, is primarily to apply a clamping pressure for fixing the test specimen during the test method. The rolling elements of the upper shell and lower shell are preferably spheres. Preferred inert materials are SiC, $Al_2O_3$, $ZrO_2$ or WC.

The inventive test device includes a gas feed plate arranged beneath the specimen seat, with which the test gas can be conveyed to the lower side of the test specimen.

The gas feed plate is preferably is designed to be adjustable in its relative position with respect to the test specimen so that a gap width can be varied between the test specimen and the gas feed plate. By changing the gap width, a flow rate of the test gas can be modified. Thus, the flow rate of the test gas increases with a decreasing the gap width. The gas feed plate in this case can also be coupled with a suitable actuator, which makes it possible to change the gap width during the test method in order to emulate real use conditions of the test specimen being tested.

The gas feed plate can sit on a hollow ram, via which the das test gas is conveyed to the gas feed plate. The gas feed plate then includes in particular a centrically arranged exit opening for the test gas and grooves arranged concentrically around the exit opening. The advantage of the presettable groove texture of the upper side of the gas feed plate facing the test specimen is that the gas is fed turbulently and it is not possible for local enrichments of evaporating components from the base material of the specimen to form.

The inventive test device also includes a ram arranged above the specimen seat, with which a presettable mechanical load can be exerted on the upper side of the test specimen. During the test method, the ram accordingly presses on the test specimen from the upper side. The ram can also be coupled with a suitable actuator so that the mechanical load can be varied during the test method.

The ram preferably includes a gas line, through which the test gas or an inert gas is conveyed to the upper side of the test specimen. This further increases the variability of the test device and the test method performed with it.

It is furthermore preferred if the ram has a spherical shape on the load initiation and is made of an inert and elastic material. Therefore, it is provided that a ductile foil, e.g., a gold foil, be applied in the area of the tip of the ram to avoid punctiform load initiation.

A further aspect of the invention lies in making available a method for simultaneously exposing a disk-shaped test specimen to a flowing and pressurized test gas and mechanical load. The method is comprised of the following steps:
(i) Making available a test device, comprised of:
   a specimen seat, which is designed in such a way that an edge area of the test specimen rests on the specimen seat and an inner area of the test specimen is accessible from its upper side and lower side;
   a ram arranged above the specimen seat, with which a presettable mechanical load can be exerted on the upper side of the test specimen; and
   a gas feed plate arranged beneath the specimen seat, with which the test gas can be conveyed to a lower side of the test specimen;
(ii) Making available the disk-shaped test specimen;
(iii) Inserting the test specimen into the test device; and
(iv) Exposing an upper side of the test specimen with a presettable load as well as simultaneously subjecting a lower side of the test specimen with the flow of the test gas.

In step (i), the test device described in the foregoing is made available. Making available naturally also includes producing operational readiness, i.e., among other things, connecting the test gas as well as ensuring the power supply to the available electrical consumers in the test device among other things.

In step (ii), a disk-shaped test specimen is made available. The test specimen is preferably 1 to 5 mm thick. The length and width or diameter of the test specimen should be adapted to the conditions of the test device. The test specimen should be designed as much as possible so that a deformation in the course of the load initiation produces approximately 1% linear expansion. Many metallic materials are already available as sheet metal, which, for the inventive test method, then only has to be cut correctly into the appropriate shape for the concrete test device. As a result, producing the test specimen is very cost-effective.

In step (iii), the test specimen is inserted into the test device. This normally includes opening the test device and placing the test specimen on the specimen seat.

Finally in step (iv), the upper side of the test specimen is exposed to a presettable load, while the test gas is simultaneously fed from the lower side of the test specimen.

According to a preferred embodiment of the method, the specimen seat, the ram and the gas feed plate are arranged in the interior of a pressure-resistant test container. Step (iv) takes place under the application of pressure. In other words, a further parameter is available for formulating the test method, namely the total pressure.

In step (iv), a temperature of the test specimen lies preferably in a range of $-50°$ C. to $850°$ C. Furthermore, a temperature of the test gas in step (iv) lies preferably in the range of $-50°$ C. to $1000°$ C. Suitable means for adjusting the temperatures are sufficiently known so that a more detail described thereof will be dispensed with. As a result, two additional parameters are available that further increase the variability of the test method.

Moreover, it is preferred if a flow rate of the test gas is adjusted by changing the gas mass flow and the gap width between the gas feed plate and the test specimen. The flow rate of the test gas lies in this case in particular at 0.1 m/s to 100 m/s.

A preferred variation of the method procedure provides in step (iv) for one or more of the variables of flow rate of the test gas, temperature of the test specimen, temperature of the test gas, pressure and mechanical load to be changed during execution of the method.

DESCRIPTION OF THE DRAWINGS

The invention is described in greater detail in the following in an exemplary embodiment and on the basis of the associated drawings. The drawings show.

DETAILED DESCRIPTION OF THE INVENTION

Figure 1:
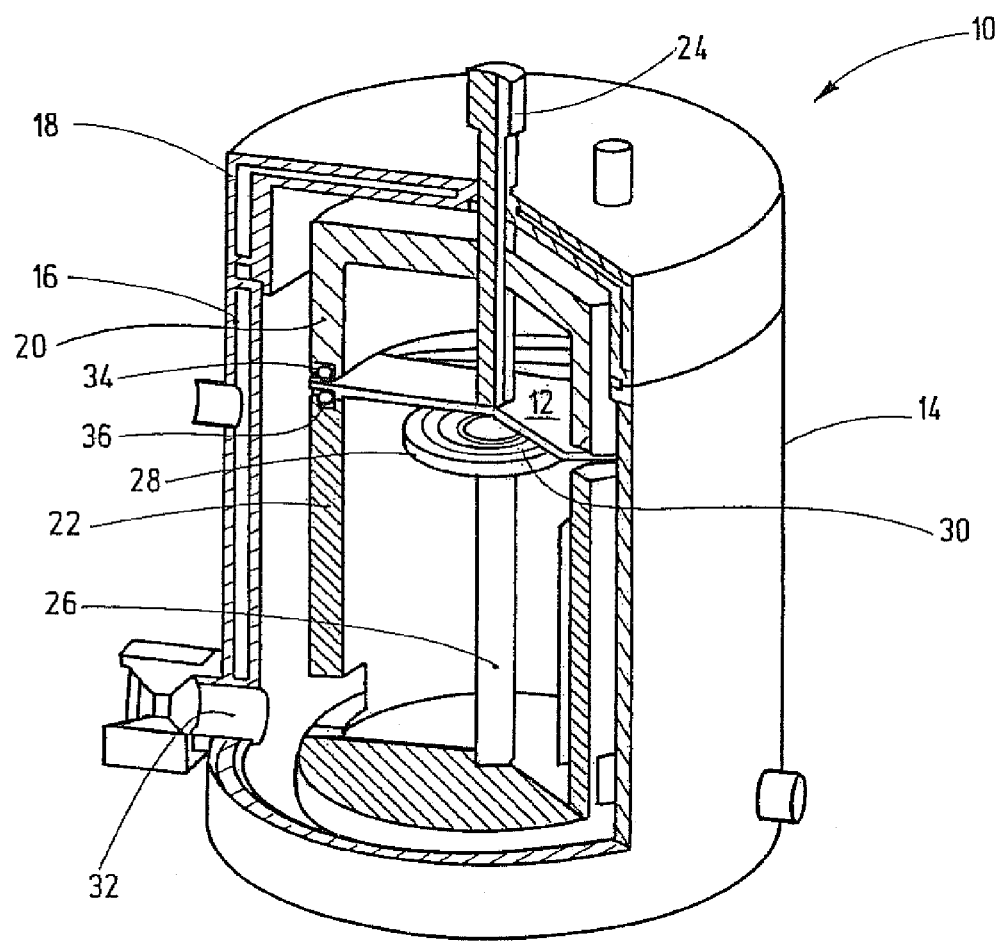
FIG. 1 A three-dimensional sectional view of an inventive testing device.
Figure 2:
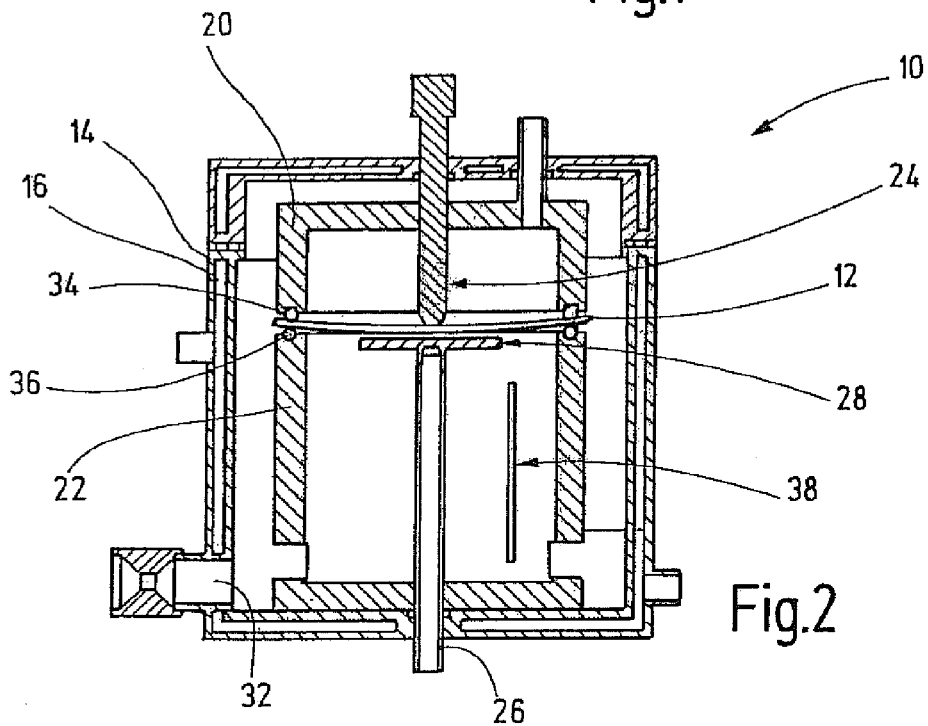
FIG. 2 A two-dimensional sectional view of the testing device from FIG. 1.

FIGS. 1 and 2 show different sectional representations of a test device 10 for simultaneously exposing a disk-shaped test specimen 12 to a test gas (as a rule a flowing and pressurized corrosive gas) and mechanical load.

As shown here, the test specimen 12 is available as a circular disk made of the to-be-tested material, for example a metallic material. Producing these types of test specimens 12 for the test device 10 can be realized in a simple manner with the aid of known processing methods so that it is possible at this point to dispense with a more detailed explanation.

The test device 10 is designed as a pressure-resistant test container 14, configured in this case of two elements with a vessel 16 and an associated cover 18. The vessel 16 as well as the cover 18 contains a double jacket that can be permeated by a coolant. The coolant can be water for example, which circulates via a thermostat (not shown in this case).

Located in the interior of the test container 14 is an inner container comprised of an upper shell and a lower shell 20, 22. The inner container defines a specimen chamber, in which the test specimen 12 is arranged for execution of the test method.

A ram 24 is guided approximately centrically through the cover 18 of the test container 14 and the upper shell 20. A presettable load is exerted on the test specimen 12 via the ram 24.

The vessel 16 of the test container 14 and the lower shell 22 also have a breakthrough in the center, through which a hollow ram 26 is guided, whose exit opening discharges approximately centrically in a gas feed plate 28. The test gas is conveyed to the gas feed plate 28 with the hollow ram 26.

The gas feed plate 28 has a plurality of grooves 30, which are arranged radially circumferentially around the exit opening of the hollow ram 26 on an upper side of the gas feed plate 28. The hollow ram 26 is furthermore displaceably mounted so that a gap width can be adjusted between the gas feed plate 28 and test specimen 12. The test gas entering through the inlet opening in the area of the gas feed plate 28 thus flows into the gap specified by the test specimen 12 and the gas feed plate 28 and enters from there into a lower area of the specimen chamber in order to exit the test device 10 again via an exit opening 32.

The test specimen 12 is fixed on a specimen seat during execution of the test method. This specimen seat is comprised in this case of rolling elements 34, 36 sitting on the upper shell as well as the lower shell 20, 22, in this case in the form of spheres made of SiC. The rolling elements 34, 36 are arranged on the edges of the upper shell and the lower shell 20, 22 (approximately in the manner of a roller bearing). When the test specimen 12 is subjected to a mechanical load, the test specimen 12 can be bent in the direction of the center without tensile stress of a considerably degree occurring, because it slides on its side edges along the rolling elements 34, 36. As a result, a radially symmetrical distribution of stress is assured during the test method.

In the following a method for simultaneously exposing the disk-shaped test specimen 12 to a test gas and mechanical load utilizing the previously described test device 10 will be described in greater detail.

To begin with, the test container 14 is opened and the test specimen 12 is placed on the rolling elements 36 of the lower shell 22. After closing, the rolling elements 34 are also adjacent to the upper shell 20 on the test piece 12 and apply an additional clamping force in order to secure the test specimen 12 against displacement during execution of the test method.

The test specimen 12 is now acted upon by the ram 24 having a presettable load. Typically, loads of up to 150 megapascal or the load equivalent of 1% linear expansion are prescribed. It should be noted that the ram 24 can also be moved by an actuator (not shown in this case) during execution of the method in order to vary the load initiation and thereby emulate a load situation that more closely approximates the actual component as the case may be.

The loaded test specimen 12 is now subjected to the flow of the test gas from its lower side. If applicable, the ram 24 can also include a gas supply feed for the load initiation, via which the test gas can be fed supplementally to the upper side of the test specimen 12.

The test gas is conveyed in every case through the hollow ram 26 to a centrically situated exit opening of the gas feed plate 28. By specifying the gas mass flow and adjusting the gap width between the gas feed plate 28 and the test specimen 12, the flow rate of the test gas on the test specimen 12 can be set. In this case as well, by changing the gap width and/or changing the gas mass flow, a variation can be effected if applicable during execution of the test method.

After exiting the gap, the test gas passes through the portion of the specimen chamber located beneath the gas feed plate 28 and in the process can for example flow around a second test specimen 38 introduced for comparison purposes, which is not subject to a mechanical load. The test gas then exits the test container 14 via the exit opening 32.

LIST OF REFERENCE NUMBERS

10 Test device
12 Test specimen
14 Test container
16 Vessel
18 Cover
20 Upper shell
22 Lower shell
24 Ram
26 Hollow ram
28 Gas feed plate
30 Grooves
32 Exit opening
34, 36 Rolling elements
38 Second test specimen

We claim:

1. A test device for simultaneously exposing a disk-shaped test specimen to a flowing and pressurized test gas and mechanical load, comprised of the following components:
   a specimen seat, which is designed in such a way that an edge area of the disk-shaped test specimen rests on the specimen seat and an inner area of the test specimen is accessible from its upper side and exterior lower side;
   a ram arranged above the specimen seat, with which a presettable mechanical load can be exerted on the upper side of the test specimen; and
   a gas feed plate arranged beneath the specimen seat, with which the test gas can be conveyed to the exterior lower side of the test specimen.

2. The test device according to claim 1, wherein the specimen seat, the ram and the gas feed plate are arranged in the interior of a pressure-resistant test container.

3. The test device according to claim 2, wherein the test container makes available a specimen chamber, which accommodates the gas feed plate and includes a gas exit opening arranged beneath the gas feed plate.

4. The test device according to claim 2, wherein the test container has a double jacket as an outer shell that can be permeated by a coolant.

5. The test device according to claim 2, wherein the test device contains a lower shell, which accommodates the gas feed plate, and the specimen seat includes rolling elements made of an inert material sitting on an edge of the lower shell.

6. The test device according to claim 5, wherein the test device contains an upper shell, which accommodates the ram, and the specimen seat includes rolling elements made of an inert material sitting on an edge of the upper shell.

7. The test device according to claim 5, wherein rolling elements are spheres.

8. The test device according to claim 1, wherein the gas feed plate is designed to be adjustable in its relative position with respect to the test specimen so that a gap width can be varied between the test specimen and the gas feed plate.

9. The test device according to claim 1, wherein the gas feed plate sits on a hollow ram, through which the test gas can be conveyed to the gas feed plate.

10. The test device according to claim 9, wherein the gas feed plate includes a centrically arranged exit opening for the test gas and grooves arranged concentrically around the exit opening.

11. The test device according to claim 1, wherein the ram includes a gas line, through which the test gas or an inert gas can be conveyed to the upper side of the test specimen.

12. The test device according to claim 1, wherein the ram has a spherical shape on the load initiation and is made of an inert and elastic material.

13. A method for simultaneously exposing a disk-shaped test specimen to a flowing and pressurized test gas and mechanical load, comprising:
  (i) Making available a test device, comprised of:
    a specimen seat, which is designed in such a way that an edge area of the test specimen rests on the specimen seat and an inner area of the test specimen is accessible from its upper side and exterior lower side;
    a ram arranged above the specimen seat, with which a presettable mechanical load can be exerted on the upper side of the test specimen; and
    a gas feed plate arranged beneath the specimen seat, with which the test gas can be conveyed to the exterior lower side of the test specimen;
  (ii) Making available the disk-shaped test specimen;
  (iii) Inserting the test specimen into the test device; and
  (iv) Exposing an upper side of the test specimen with a presettable load as well as simultaneously subjecting a lower side of the test specimen with the flow of the test gas.

14. The method according to claim 13, in which the specimen seat, the ram and the gas feed plate are arranged in the interior of a pressure-resistant test container and the exposing takes place under the application of pressure.

15. The method according to claim 13, in which during the exposing a temperature of the test specimen lies in a range of $-50°$ C. to $850°$ C.

16. The method according to claim 13, in which during the exposing a temperature of the test gas lies in a range of $-50°$ C. to $1000°$ C.

17. The method according to claim 13, in which a flow rate of the test gas is adjusted by changing the gas mass flow or gap width between the gas feed plate and the test specimen.

18. The method according to claim 17, in which the flow rate of the test gas lies at 0.1 m/s to 100 m/s.

19. The method according to claim 13 in which during the exposing one or several of the variables of flow rate of the test gas, temperature of the test specimen, temperature of the test gas, gas pressure and mechanical load are changed during execution of the method.

20. The method according to claim 13, wherein the gas includes a corrosive gas.

* * * * *